(12) United States Patent
Voltti

(10) Patent No.: US 11,779,424 B2
(45) Date of Patent: Oct. 10, 2023

(54) INSTRUMENT CASSETTE FOR HANDLING INSTRUMENTS

(71) Applicant: LM-INSTRUMENTS OY, Parainen (FI)

(72) Inventor: Gaius Voltti, Parainen (FI)

(73) Assignee: LM-INSTRUMENTS OY, Parainen (FI)

( * ) Notice: Subject to any disclaimer, the term of this patent is extended or adjusted under 35 U.S.C. 154(b) by 766 days.

(21) Appl. No.: 16/630,147

(22) PCT Filed: Jul. 5, 2018

(86) PCT No.: PCT/FI2018/050531
§ 371 (c)(1),
(2) Date: Jan. 10, 2020

(87) PCT Pub. No.: WO2019/012181
PCT Pub. Date: Jan. 17, 2019

(65) Prior Publication Data
US 2020/0229887 A1    Jul. 23, 2020

(30) Foreign Application Priority Data
Jul. 12, 2017    (FI) ..................... 20175681

(51) Int. Cl.
| G08B 13/14 | (2006.01) |
| B65D 83/10 | (2006.01) |
| A61B 50/30 | (2016.01) |
| A61B 90/98 | (2016.01) |
| A61C 19/02 | (2006.01) |
| A61L 2/07  | (2006.01) |
| A61L 2/26  | (2006.01) |
| G06K 19/07 | (2006.01) |

(52) U.S. Cl.
CPC .............. *A61B 50/30* (2016.02); *A61B 90/98* (2016.02); *A61C 19/02* (2013.01); *A61L 2/07* (2013.01); *A61L 2/26* (2013.01); *G06K 19/0723* (2013.01); *A61L 2202/24* (2013.01)

(58) Field of Classification Search
CPC ......... A61B 50/30; A61B 90/98; A61B 90/90; A61L 2/07; A61L 2/26; A61L 2202/24
USPC ........ 206/363, 368–370, 63.5, 565, 570–572
See application file for complete search history.

(56) References Cited

U.S. PATENT DOCUMENTS 7,268,684 B2    9/2007  Tethrake et al.
7,362,228 B2 *  4/2008  Nycz ..................... A61F 2/4657
                                            340/568.1

(Continued)

FOREIGN PATENT DOCUMENTS

WO    2008062387 A3    5/2008

*Primary Examiner* — Luan K Bui
(74) *Attorney, Agent, or Firm* — Lippes Mathias LLP

(57) ABSTRACT

An instrument cassette (100, 200, 300) for handling instruments comprises a body section (101, 201, 301) for holding the instruments and a radio frequency identifier (102, 202, 302) readable from a distance away from the instrument cassette (100, 200, 300). The radio frequency identifier (102, 202, 302) of the instrument cassette (100, 200, 300) facilitates tracing operations, such as for example disinfection, sterilization, reparation, and clinical use, directed to or carried out with a set of instruments handled with the aid of the instrument cassette (100, 200, 300). The instruments can be for example medical and/or dental hand instruments.

15 Claims, 6 Drawing Sheets

(56) References Cited

U.S. PATENT DOCUMENTS

| | | | |
|---|---|---|---|
| 8,177,776 B2 * | 5/2012 | Humayun | A61B 50/33 606/1 |
| 2006/0244597 A1 | 11/2006 | Tethrake et al. | |
| 2009/0215003 A1 * | 8/2009 | Swain | A61C 19/02 206/63.5 |
| 2011/0262250 A1 * | 10/2011 | Treat | A61B 50/30 206/370 |
| 2011/0297567 A1 * | 12/2011 | Maness | A61B 50/362 206/370 |
| 2014/0125482 A1 | 5/2014 | Rigsby et al. | |

* cited by examiner

INSTRUMENT CASSETTE FOR HANDLING INSTRUMENTS

FIELD OF THE DISCLOSURE

The disclosure relates to an instrument cassette for handling instruments which can be, for example but not necessarily, medical or dental hand instruments. The instrument cassette can be used for holding instruments for example when the instruments are sterilized by autoclaving.

BACKGROUND

In many cases, authorities and actors of the medical or dental field want to have an infallible and traceable solution to follow instruments to be able to trace disinfection, sterilization, reparation, clinical use, and other operations targeted to or carried out with the instruments under consideration. Nowadays, users do not typically have the time and willingness to generate reports manually because of the related workload. In addition, there is a risk of errors with manual data recording and identification of instruments, which prevents regarding the manually recorded data as an irrefutable proof of what has been done and what has been not done.

A known solution for tracing operations directed to or carried out with instruments is to provide each instrument with a unique identifier such as e.g. radio frequency identifier "RFID". For example, publication WO2008062387 describes an instrument comprising a radio frequency identifier. The radio frequency identifier is embedded in a polymer sheet that is attached on a surface of the handle of the instrument. The polymer sheet that includes the radio frequency identifier can be, for example, wrapped around the handle of the instrument. In order to obtain an even surface, it is possible to provide the instrument with a recess corresponding in size to the polymer sheet. In an advantageous embodiment described in WO2008062387, the polymer sheet comprises two layers between which the radio frequency identifier is located. In many cases, there can be however a need to trace operations directed to or carried out with particular instrument sets. Thus, there is a need for additional technical solutions for being able to trace operations directed to or carried out with instrument sets.

SUMMARY

The following presents a simplified summary in order to provide a basic understanding of some embodiments of the invention. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In many cases, instruments are handled with the aid of instrument cassettes each of which is suitable for holding a set of instruments during e.g. an autoclaving sterilization process. An instrument set placed in an instrument cassette may comprise for example medical and/or dental hand instruments needed for carrying out given measures.

In accordance with the invention, there is provided a new instrument cassette for handling instruments such as for example medical or dental hand instruments.

The instrument cassette comprises:
a body section for holding instruments, and
a radio frequency identifier "RFID" that is readable from a distance away from the radio frequency identifier.

The radio frequency identifier of the instrument cassette facilitates tracing operations, such as e.g. disinfection, sterilization, reparation, and clinical use, directed to or carried out with a set of instruments handled with the aid of the instrument cassette.

A number of exemplifying and non-limiting embodiments are described in accompanied dependent claims.

Various exemplifying and non-limiting embodiments both as to constructions and to methods of operation, together with additional objects and advantages thereof, will be best understood from the following description of specific exemplifying and non-limiting embodiments when read in connection with the accompanying drawings.

The verbs "to comprise" and "to include" are used in this document as open limitations that neither exclude nor require the existence of un-recited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

Exemplifying and non-limiting embodiments and their advantages are explained in greater detail below in the sense of examples and with reference to the accompanying drawings, in which.

DESCRIPTION OF EXEMPLIFYING AND NON-LIMITING EMBODIMENTS

The specific examples provided in the description below should not be construed as limiting the scope and/or the applicability of the accompanied claims. Lists and groups of examples provided in the description are not exhaustive unless otherwise explicitly stated.

Figure 1A:
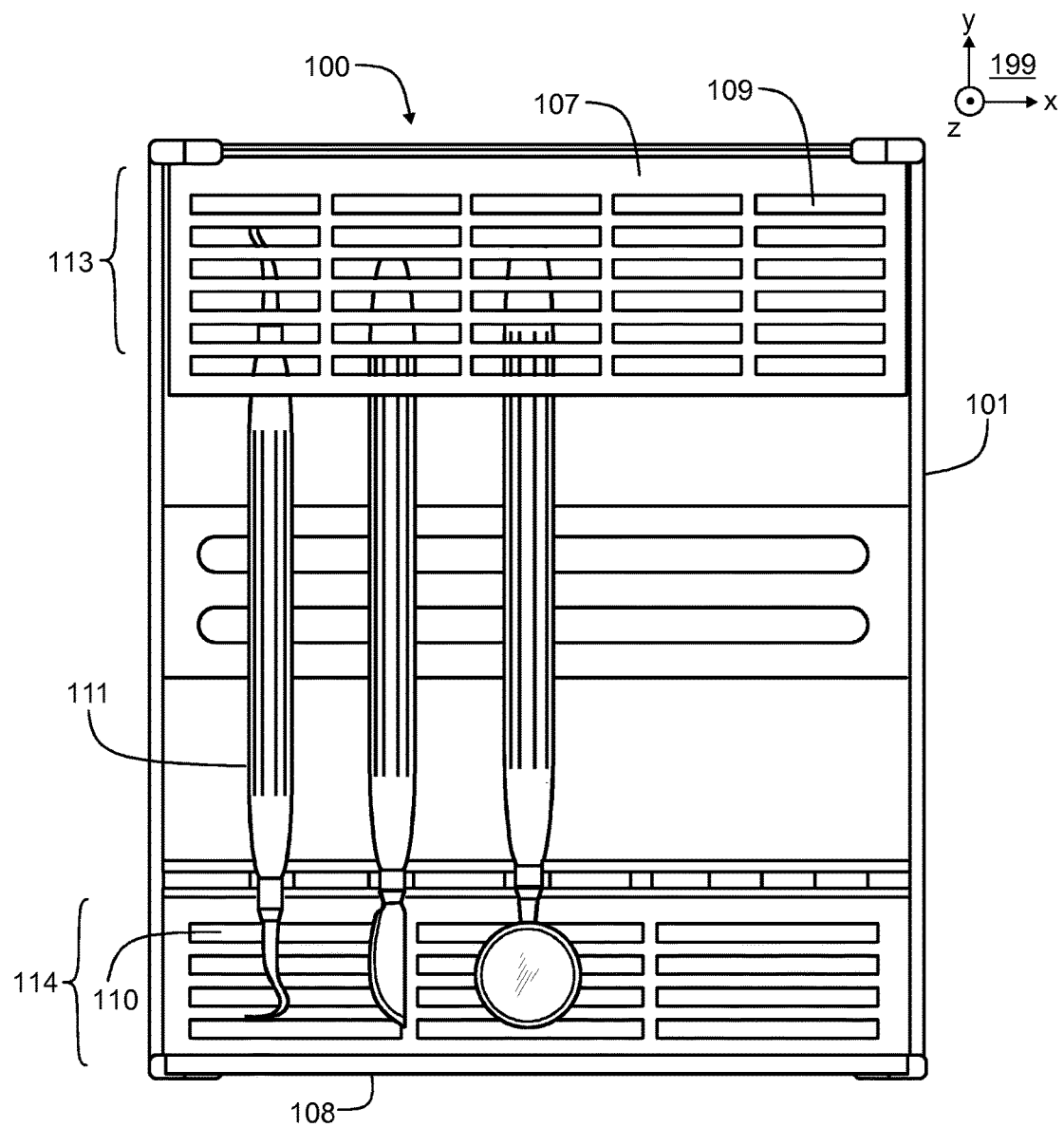
FIGS. 1a, 1b, 1c, 1d, and 1e illustrate an instrument cassette according to an exemplifying and non-limiting embodiment.
Figure 1B:
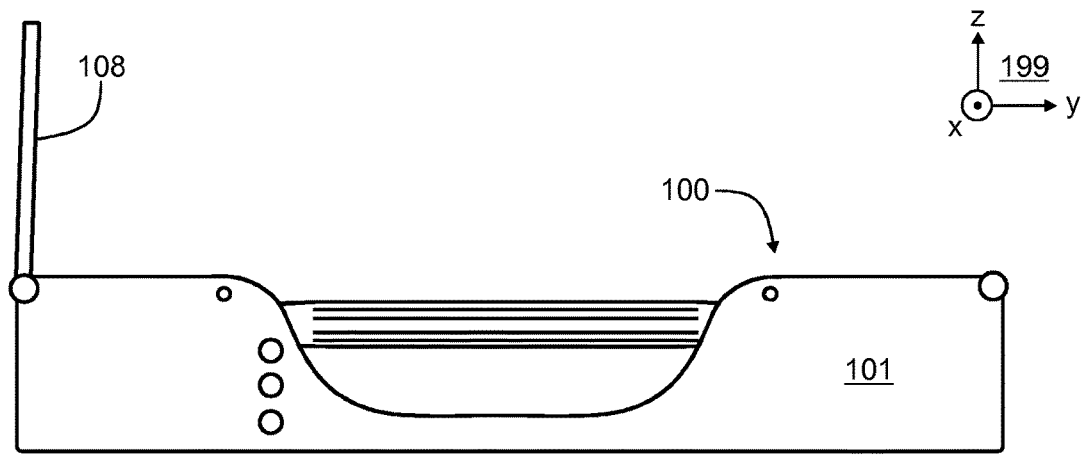
Figure 1C:
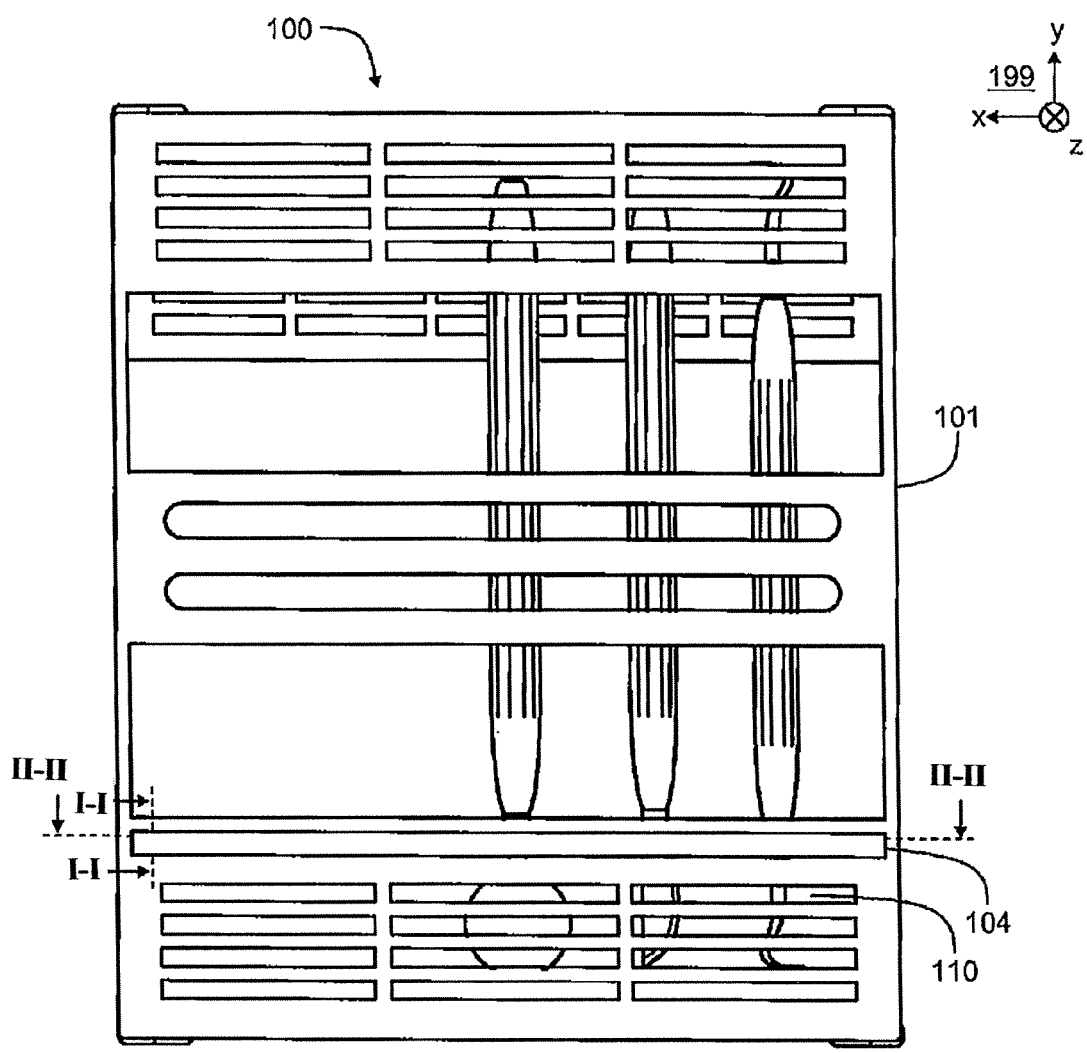
Figure 1D:
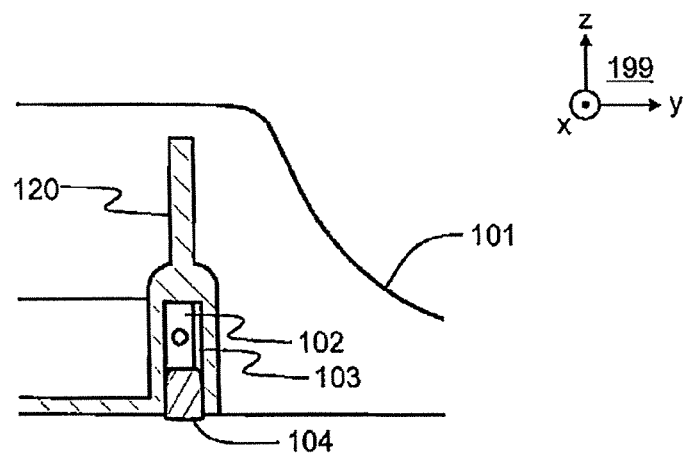
Figure 1E:
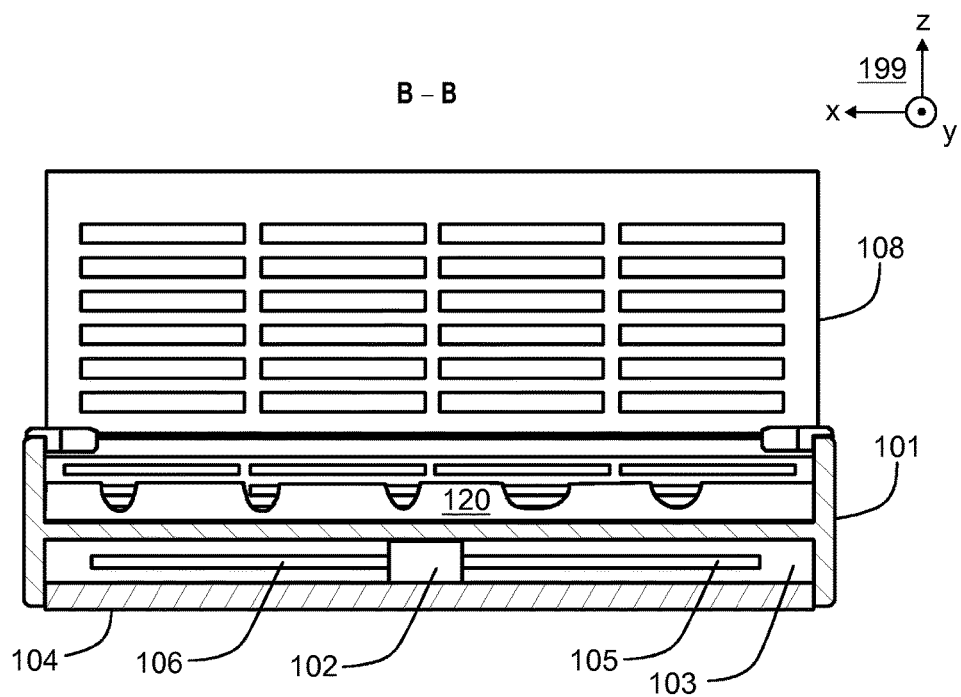

FIGS. 1a, 1b, 1c, 1d, and 1e illustrate an instrument cassette 100 according to an exemplifying and non-limiting embodiment. FIG. 1a shows a top view of the instrument cassette, FIG. 1b shows a side view of the instrument cassette, FIG. 1c shows a bottom view instrument cassette, FIG. 1d shows a view of a section taken along a line I-I shown in FIG. 1c, and FIG. 1e shows a view of a section taken along a line II-II shown in FIG. 1c. The section plane related to FIG. 1d is parallel with the yz-plane of a coordinate system 199, and the section plane related to FIG. 1e is parallel with the xz-plane of the coordinate system 199. The instrument cassette 100 comprises a body section 101 for holding instruments such as e.g. medical or dental hand instruments. In the exemplifying situation shown in FIGS. 1a-1c, there are three exemplifying instruments in the instrument cassette 100. One of the exemplifying instruments is denoted with a reference 111. The instruments are not shown in the section views shown in FIGS. 1d and 1e. The exemplifying instrument cassette 100 comprises two sections 113 and 114 for the operational portions of the instruments. An operational portion can be for example a blade of a knife. It is, however, also possible that there is only one section for operational portions of instruments. The material of the body section 101 is advantageously electrically non-conductive so that radio frequency radiation can penetrate the material of the body section. The material of the body section 101 may comprise for example plastic that may comprise e.g. polyphenylene sulfide "PPS". The instrument cassette 100 comprises cover elements 107 and 108 for covering the rooms for containing the operational portions of the instruments so as to prevent unintentional touching the operational portions of the instruments. In the exemplifying instrument cassette 100, the cover elements 107 and 108 are hinged to the body section 101. It is, however, also possible that a cover element or cover elements is/are shape locked or otherwise mechanically connected to a body section of an instrument cassette according to an exemplifying embodiment. It is also possible that an instrument cassette according to an exemplifying embodiment does not comprise any cover element of the kind mentioned above. In the exemplifying situation shown in FIGS. 1a and 1b, the cover element 108 is in an opened position. The cover elements 107 and 108 are advantageously provided with apertures which facilitate hot vapor to get in contact with the operational portions of the instruments during an autoclaving sterilization process. In FIG. 1a, one of the apertures of the cover element 107 is denoted with a reference 109. Correspondingly, the bottoms of the sections 113 and 114 for containing the operational portions of the instruments are advantageously provided with apertures. In FIGS. 1a and 1c, one of the apertures of the bottom of the section 114 is depicted with a reference 110. Furthermore, also the side walls of the sections 113 and 114 can be provided with apertures.

The instrument cassette 100 comprises a radio frequency identifier "RFID" that is readable from a distance away from the radio frequency identifier. In FIGS. 1d and 1e, the radio frequency identifier is denoted with a reference 102. In this exemplifying case, the radio frequency identifier 102 is located in a cavity 103 of the body section 101. The instrument cassette 100 comprises a closing element 104 that closes the opening of the cavity 103 and constitutes, together with the surfaces of the cavity, a room for the radio frequency identifier 102. Advantageously, the radio frequency identifier 102 is substantially not attached to the body section 101 directly but the closing element 104 keeps the radio frequency identifier 102 stationary with respect to the body section 101. In this exemplifying case, it is straightforward to replace the radio frequency identifier 102 with another radio frequency identifier after the closing element 104 has been removed. Advantageously, the closing element 104 and the surfaces of the cavity 103 constitute a hermetically sealed room for the radio frequency identifier 102. In this exemplifying case, the radio frequency identifier 102 is protected against environmental conditions such as e.g. hot vapor used in an autoclaving sterilization process. The closing element 104 can be made of flexible material that may comprise for example silicone. It is however also possible that a radio frequency identifier of an instrument cassette according to another exemplifying embodiment is attached to a surface of a cavity so that there is no need for a closing element for closing the opening of the cavity. Furthermore, it is also possible that a radio frequency identifier of an instrument cassette according to an exemplifying embodiment is attached on a surface of the body section or another element of the instrument cassette so that the radio frequency identifier is not in a cavity or similar.

The radio frequency identifier 104 can be, for example but not necessarily, a ceramic radio frequency identifier tag. The radio frequency identifier 102 may comprise, for example but not necessarily, a memory circuit capable of storing digital information. The digital information may contain for example identifying information identifying the instrument cassette 100 as an individual object from among similar instrument cassettes and/or information indicating e.g. the date of manufacture of the instrument cassette, the manufacturer of the instrument cassette and/or other information related directly or indirectly to the instrument cassette. Furthermore, the digital information may indicate the number of sterilization cycles carried out using the instrument cassette 100. It is, however, also possible that the radio frequency identifier 102 does not comprise any memory circuit but identification information related to the radio frequency identifier 102 is represented by e.g. radiation properties of the radio frequency identifier 102.

In the exemplifying instrument cassette 100 illustrated in FIGS. 1a-1e, the cavity 103 is an elongated groove. The radio frequency identifier 102 comprises an elongated antenna structure, and the closing element 104 is an elongated bar arranged to close the elongated groove. The elongated antenna structure of the radio frequency identifier 102 is illustrated in FIG. 1e where elements of the antenna structure are denoted with references 105 and 106. The antenna structure can be e.g. a dipole antenna. As illustrated in FIGS. 1d and 1e, the opening of the elongated cavity faces downwards when the instrument cassette is in its operating position. As illustrated in FIGS. 1d and 1e, a part 120 of the body section for mechanically supporting instruments is shaped to constitute the elongated cavity. This construction is a straightforward way to implement the elongated cavity for the radio frequency identifier 102. It is also possible that an elongated cavity has its opening on a side wall of the instrument cassette, i.e. the elongated cavity constitutes an elongated tubular room.

It is, however, also possible that a radio frequency identifier of an instrument cassette according to an exemplifying embodiment does not comprise an elongated antenna structure of the kind shown in FIG. 1e. In this exemplifying case, the shape of a cavity for containing the radio frequency identifier may differ from the shape of the cavity 103 shown in FIGS. 1d and 1e.

Figure 2A:
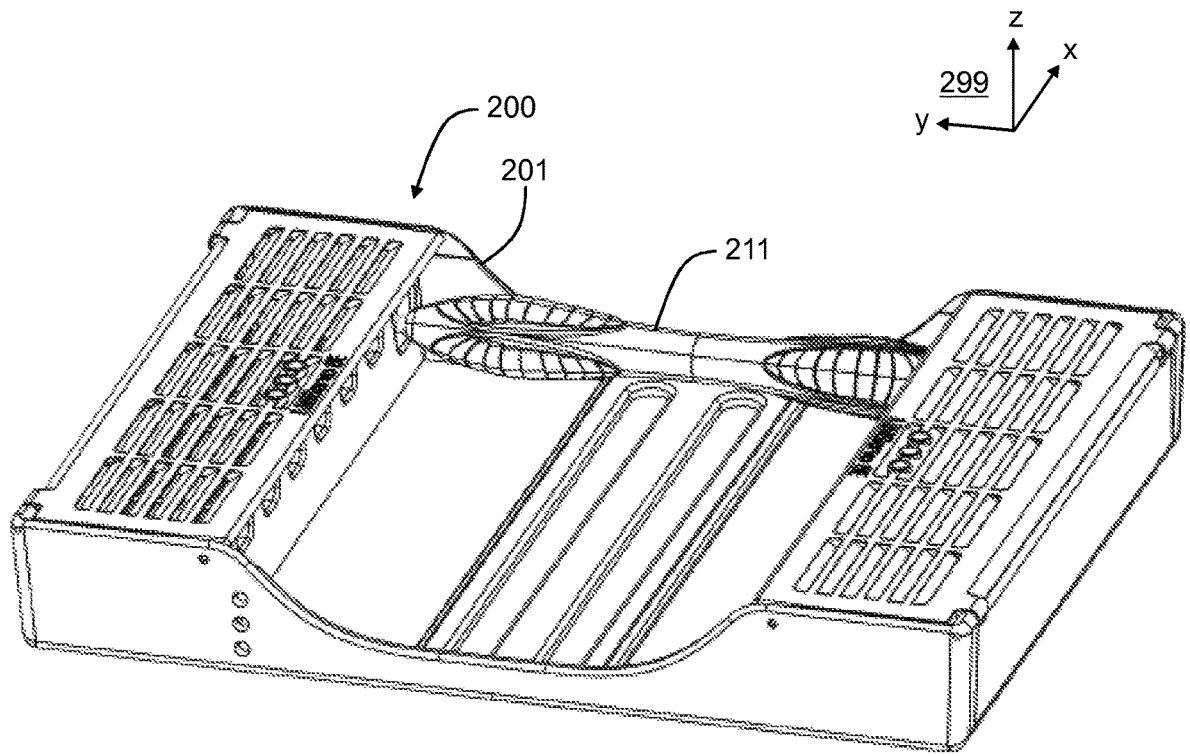
FIGS. 2a, 2b, 2c, and 2d illustrate an instrument cassette according to an exemplifying and non-limiting embodiment and a process for installing a radio frequency identifier "RFID" in the instrument cassette.
Figure 2B:
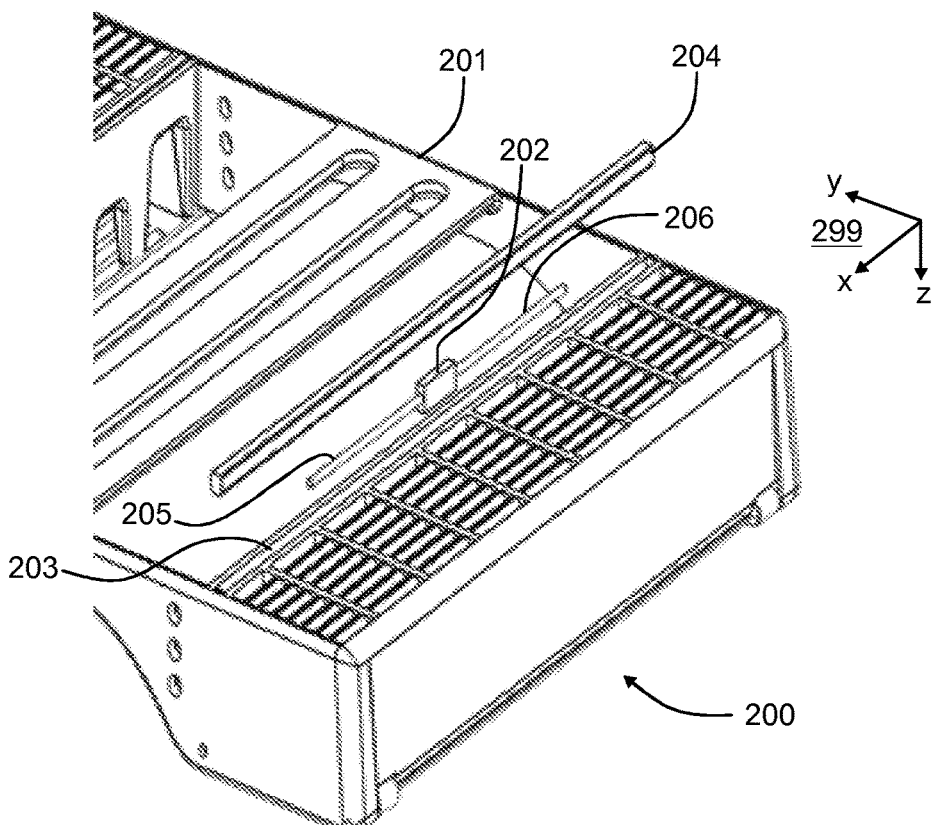
Figure 2C:
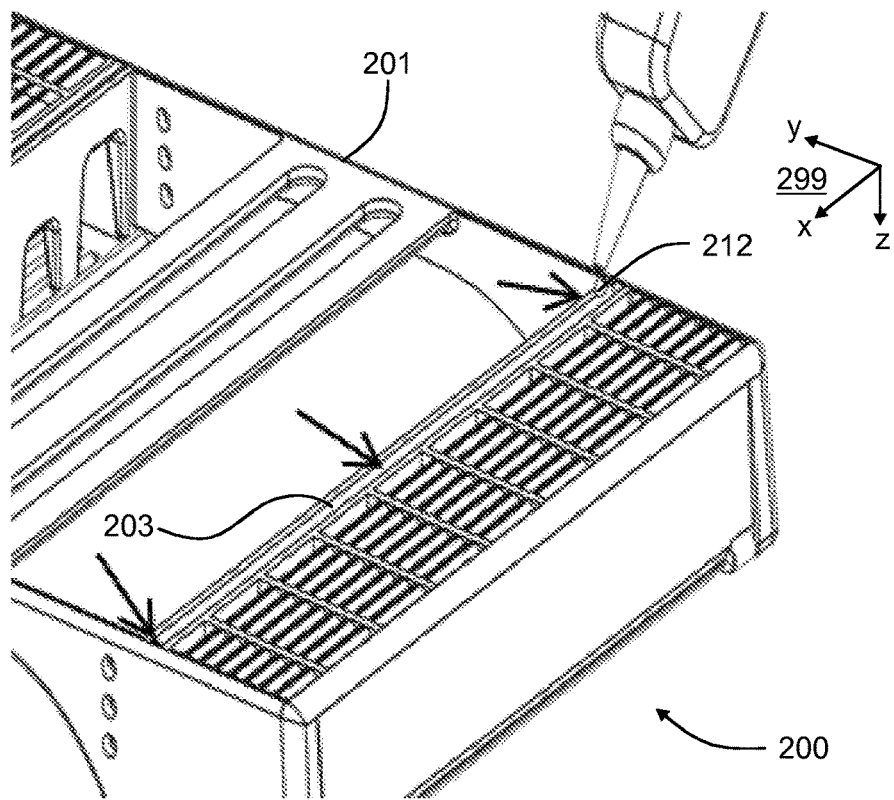
Figure 2D:
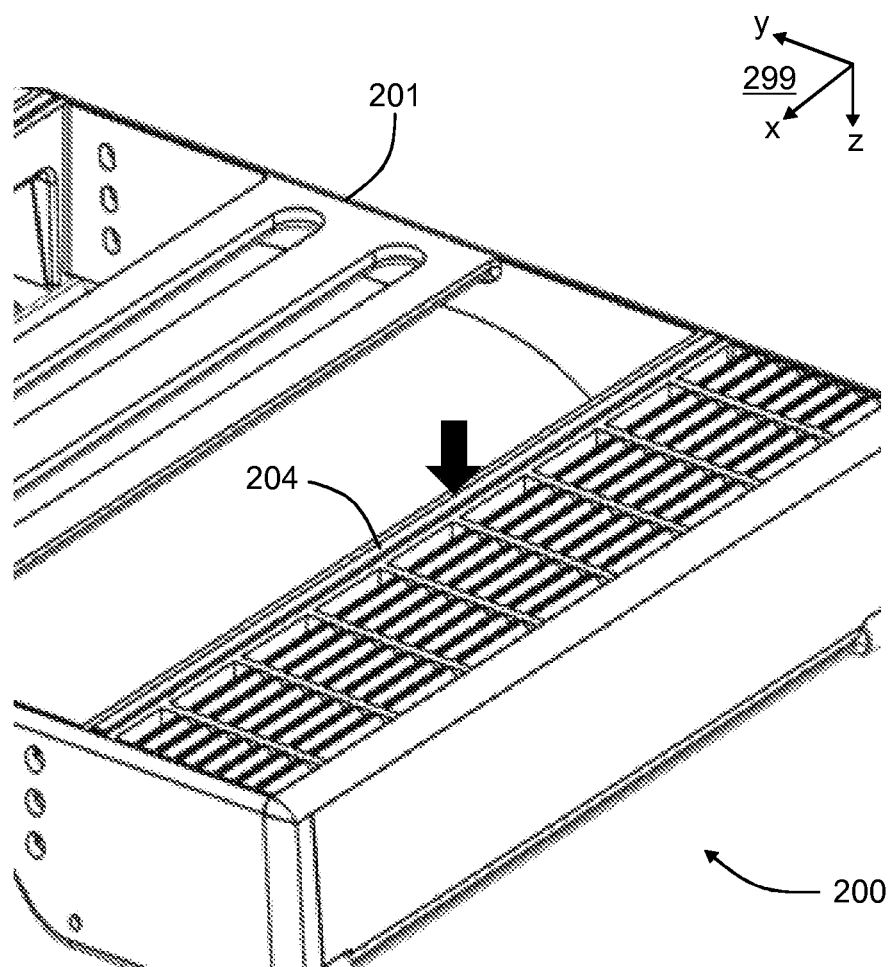

FIGS. 2a, 2b, 2c, and 2d illustrate an instrument cassette 200 according to an exemplifying and non-limiting embodiment. The viewing directions related to FIGS. 2a-2d are illustrated with a coordinate system 299. In the exemplifying situation shown in FIG. 2a, there is an instrument 211 in the instrument cassette 200. FIGS. 2b, 2c, and 2d illustrate a process for installing a radio frequency identifier "RFID" 202 in the instrument cassette 200. The instrument cassette 200 comprises a body section 201 for holding instruments. As illustrated in FIG. 2b, the body section 201 has a cavity 203 for the radio frequency identifier 202. As can be understood based on FIG. 2b, the radio frequency identifier 202 is easy to install because the radio frequency identifier can be dropped to the cavity 203 and the cavity provides a mechanical support for the radio frequency identifier 202 during later phases of the assembly work. In this exemplifying case, the instrument cassette 200 comprises a closing element 204 that is suitable for closing the opening of the cavity, keeping the radio frequency identifier stationary with respect to the surfaces of the cavity, and constituting, together with the surfaces of the cavity 203, a room for the radio frequency identifier 202. The room for the radio frequency identifier 202 is advantageously a hermetically sealed room. In this exemplifying case, the cavity 203 is an elongated groove, the radio frequency identifier comprises an elongated antenna structure 205 and 206, and the closing element 205 is an elongated bar for closing the elongated groove. The closing element 204 is advantageously flexible, and the cavity 203 and the flexible closing element 204 are advantageously dimensioned so that the flexible closing element gets compressed in response to insertion in the cavity 203 in order to achieve an appropriate sealing.

In the exemplifying installation process illustrated in FIGS. 2b-2d, the closing element 204 is attached with glue to the surfaces of the cavity 203 in order to secure the fastening of the closing element 204. Arrows shown in FIG. 2c illustrate an exemplifying case where glue is added to the both ends and to the middle of the elongated cavity 203. A droplet of the glue is denoted with a reference 212. In cases where the glue is spread smoothly over contact surfaces of the closing element 204, the glue can act also as a seal for sealing the room containing the radio frequency identifier 202. In many cases, it is advantageous to use suitable primer with the glue. After the glue has been added, the closing element 204 can be pushed to the cavity 203. This is illustrated with an arrow shown in FIG. 2d. A spatula or an element having a flat surface can be used for ensuring that the closing element 204 positions itself properly.

In the exemplifying instrument cassette 200 illustrated in FIGS. 2a-2d, the closing element 204 is a pre-manufactured element that is installed in the body section 201 of the instrument cassette. It is also possible that a closing element of an instrument cassette according to an exemplifying embodiment is formed by material which has been cast in the opening of a cavity after a radio frequency identifier has been inserted in the cavity.

Figures 3A, 3B:
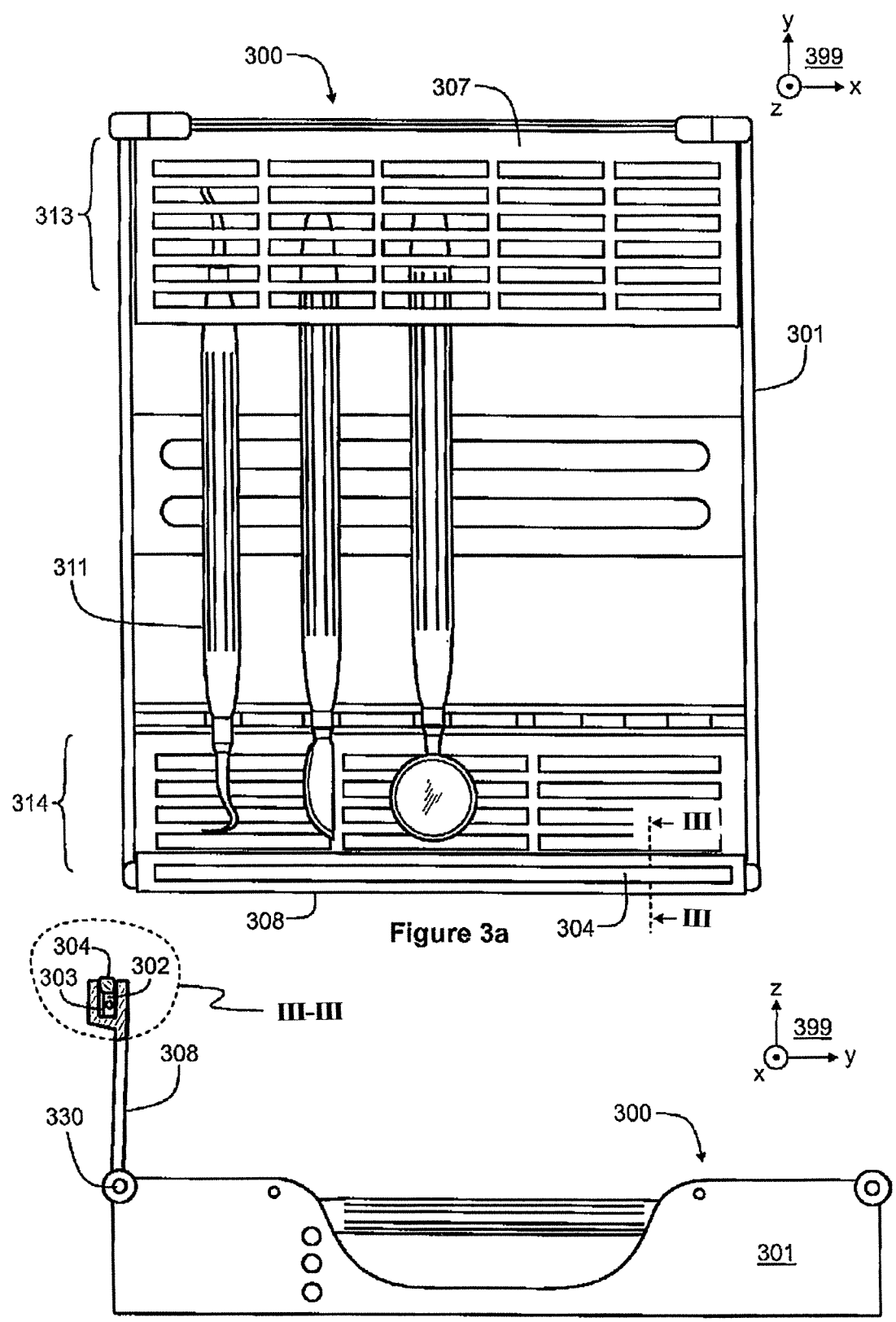
FIGS. 3a and 3b illustrate an instrument cassette according to an exemplifying and non-limiting embodiment.

FIGS. 3a and 3b illustrate an instrument cassette 300 according to an exemplifying and non-limiting embodiment. FIG. 3a shows a top view of the instrument cassette, and FIG. 3b shows a side view of the instrument cassette. Furthermore, FIG. 3b shows a view of a partial section taken along a line III-III shown in FIG. 3a. The section plane related to the partial section shown in FIG. 3b is parallel with the yz-plane of a coordinate system 399. The instrument cassette 300 comprises a body section 301 for holding instruments such as e.g. medical or dental hand instruments. In the exemplifying situation shown in FIGS. 3a and 3b, there are three exemplifying instruments in the instrument cassette 300. One of the exemplifying instruments is denoted with a reference 311. The exemplifying instrument cassette 300 comprises two sections 313 and 314 for the operational portions of the instruments. The instrument cassette 300 comprises cover elements 307 and 308 for covering the rooms for containing the operational portions of the instruments so as to prevent unintentional touching the operational portions of the instruments. In the exemplifying instrument cassette 300, the cover elements 307 and 308 are hinged to the body section 301. It is, however, also possible that a cover element or cover elements is/are shape locked or otherwise mechanically connected to a body section of an instrument cassette according to an exemplifying embodiment. In the exemplifying situation shown in FIGS. 3a and 3b, the cover element 308 is in an opened position.

The instrument cassette 300 comprises a radio frequency identifier "RFID" that is readable from a distance away from the radio frequency identifier. In FIG. 3b, the radio frequency identifier is denoted with a reference 302. In this exemplifying case, the radio frequency identifier 302 is located in a cavity 303 of the cover element 308. The instrument cassette 300 comprises a closing element 304 that closes the opening of the cavity 303 and constitutes, together with the surfaces of the cavity, a room for the radio frequency identifier 302. Advantageously, the cover element 308 is non-destructively detachable from the body section 301. In other words, the cover element 308 can removed without a need for irreversible material deformations. In this exemplifying case, the cover element 308 can be detached from the body section 301 by removing a hinge pin 330. As the cover element 308 is non-destructively detachable from the body section 301, it is straightforward to replace the cover element 308 with another cover element that is provided with another radio frequency identifier. Thus, the radio frequency identifier 302 can be easily replaced with another radio frequency identifier.

In the exemplifying instrument cassettes 100, 200, and 300 illustrated in FIGS. 1a-1e, 2a-2d, and 3a and 3b, the radio frequency identifier is located in a cavity constituted by the body section or in a cavity constituted by a cover element for preventing unintentional touching the operational portions of instruments. It is also possible that a radio frequency identifier is located in a part of the instrument cassette that is neither the above-mentioned body section nor a cover element of the kind mentioned above. The part can be for example a module for containing a radio frequency identifier. The module can be attached to e.g. the body section with a suitable attaching arrangement. The attaching arrangement may comprise for example a screw and/or it can be based on material elasticity and/or spring force so that the module is easy to remove and to replace with another module.

The specific examples provided in the description given above should not be construed as limiting the scope and/or the applicability of the appended claims. Lists and groups of examples provided in the description given above are not exhaustive unless otherwise explicitly stated.

What is claimed is:

1. An instrument cassette for handling dental instruments, the instrument cassette comprising a body section comprised of an electrically non-conducting material for holding the instruments and a radio frequency identifier readable from a distance away from the radio frequency identifier, wherein the body section constitutes a cavity, the radio frequency identifier is located in the cavity, and an opening of the cavity is on a bottom of the body section and on an opposite side with respect to a room for containing the instruments, and wherein a wall extends vertically from a top of the body section, said wall including at least one recess for mechanically supporting the instruments, and wherein said wall at a base region includes the cavity.

2. An instrument cassette according to claim 1, wherein the instrument cassette further comprises a closing element closing an opening of the cavity.

3. An instrument cassette according to claim 2, wherein the closing element is arranged to keep the radio frequency identifier stationary with respect to the part of the instrument cassette constituting the cavity, the radio frequency identifier becoming loose with respect to the part of the instrument cassette in response to removal of the closing element.

4. An instrument cassette according to claim 3, wherein the closing element and surfaces of the cavity constitute a hermetically sealed room for the radio frequency identifier.

5. An instrument cassette according to claim 1, wherein the cavity is an elongated groove and the radio frequency identifier comprises an elongated antenna structure.

6. An instrument cassette according to claim 2, wherein the cavity is an elongated groove, the radio frequency identifier comprises an elongated antenna structure, and the closing element is an elongated bar closing the elongated groove.

7. An instrument cassette according to claim 1, wherein the instrument cassette further comprises a cover element for covering a room for containing operational portions of the instruments so as to prevent unintentional touching the operational portions of the instruments.

8. An instrument cassette according to claim 1, wherein the part of the instrument cassette constituting the cavity is non-destructively detachable from the body section.

9. An instrument cassette according to claim 2, wherein the closing element is attached with glue to the surfaces of the cavity.

10. An instrument cassette according to claim 3, wherein the closing element is formed by material cast in the opening of the cavity after the radio frequency identifier has been inserted in the cavity.

11. An instrument cassette according to claim 1, wherein the material of the body section comprises plastic.

12. An instrument cassette according to claim 11, wherein the plastic comprises polyphenylene sulfide "PPS".

13. An instrument cassette according to claim 2, wherein the closing element is made of flexible material.

14. An instrument cassette according to claim 13, wherein the flexible material comprises silicone.

15. An instrument cassette according to claim 13, wherein the cavity and the flexible closing element are dimensioned so that the flexible closing element gets compressed in response to insertion in the cavity.

* * * * *